United States Patent [19]
Dobkowski et al.

[11] Patent Number: 5,849,314
[45] Date of Patent: Dec. 15, 1998

[54] ANHYDROUS COSMETIC COMPOSITIONS

[75] Inventors: Brian John Dobkowski, Shelton; Alexander Paul Znaiden, Trumbull; Michael Charles Cheney, Fairfield; Walter Rose, New Haven, all of Conn.

[73] Assignee: Chesebrough-Pond's USA Co., Division of Conopco, Inc., Greenwich, Conn.

[21] Appl. No.: 821,133

[22] Filed: Mar. 20, 1997

Related U.S. Application Data

[60] Provisional application No. 60/020,745 Jun. 28, 1996.

[51] Int. Cl.$^6$ .......................................................... A61K 7/43
[52] U.S. Cl. ............................... 424/401; 424/59; 424/60; 514/887
[58] Field of Search ................................. 424/401, 59, 60; 514/887

[56] References Cited

U.S. PATENT DOCUMENTS 5,654,362  8/1997  Schulz, Jr. et al. ...................... 524/862

FOREIGN PATENT DOCUMENTS 03-197413  8/1991  Japan .
97/44010  11/1997  WIPO ............................... A61K 7/48

OTHER PUBLICATIONS

Kuroda, *Chemical Abstracts*, vol. 127, #39538, 1996.
Khaiat et al., *Chemical Abstracts*, vol. 122, #169713, 1994.
Gans et al., *Chemical Abstracts*, vol. 116, #158,925, 1992.
Hasegawa et al., *Chemical Abstracts*, vol. 126, #229389, 1996.

*Primary Examiner*—Thurman K. Page
*Assistant Examiner*—D. Faulkner
*Attorney, Agent, or Firm*—Milton L. Honig

[57] ABSTRACT

A skin treatment composition is provided which includes a crosslinked non-emulsifying siloxane elastomer, a skin conditioning agent, a volatile siloxane and no more than 5% water. Hydrocarbons such as petrolatum and polyols such as glycerin are the preferred skin conditioning agents. Inclusion of the elastomer provides a non-traditional smooth/silky feel to the skin upon application with a non-draggy rub in.

7 Claims, No Drawings

ANHYDROUS COSMETIC COMPOSITIONS

BACKGROUND OF THE INVENTION

1. Field of the Invention

The invention relates to anhydrous cosmetic compositions whose properties are enhanced by incorporation of crosslinked elastomeric silicones.

2. The Related Art

Emollients including organic esters and hydrocarbons, especially petrolatum, have long been used medicinally as skin conditioning agents. These substances are second only to water as moisturizing ingredients of choice. They function primarily as an occlusive barrier. The water content of the outer layers of human skin stratum corneum is a controlling factor in the appearance of dry skin symptoms. When the stratum corneum contains an adequate amount of water within the range of ten to twenty percent, the skin remains flexible. However, when the water content falls below ten percent the stratum corneum often becomes brittle and rough and can exhibit scaling and cracking.

The stratum corneum receives its water from the deep layers of the epidermis by diffusion or when it is brought into direct contact with water. The diffusion process is controlled by the water content of the skin as well as the concentration gradient. In a very dry environment, the water loss from the external skin layers can be significant and often exceeds the rate of replacement by diffusion. An occlusive or semi-occlusive barrier substance placed on the surface of the skin acts to retard water loss to the environment. It also allows the skin surface to rehydrate via a diffusion mechanism.

While there are many effective and economical skin conditioning agents, they nevertheless suffer from certain disadvantages.

Often the emollient types are delivered as water in oil emulsions. It is difficult to attain the critical formula balance between oil and water phases to an extent sufficient to ensure long term storage stability. One part of this critical balance is the internal phase volume. A critical volume must be obtained to maximize the chemical and physical interactions which produce and stabilize the system. If this critical volume is not balanced properly the product may suffer from viscosity change and eventual phase separation. Usually the optimum volume is quite large which limits the external phase volume size, and gives the system a draggy unfavorable slow break attribute. This critical internal phase volume restriction can reduce functionality and add unfavorable feel characteristics.

Anhydrous systems avoid emulsion stability problems. Unfortunately other aesthetic issues arise with anhydrous systems. Not all oily phase materials are compatible at high concentration. Moreover, occlusive agents such as petrolatum are relatively greasy. They suffer the disadvantage of transfer onto clothing and are not easily removed from the skin by washing with soap. Neither do they allow for adequate penetration into the epidermis.

U.S. Pat. No. 5,387,417 (Rentsch) reports obtaining cosmetically acceptable, translucent moisturizing lotions through emulsification of a petrolatum base with a crosslinked organopolysiloxane-polyoxyalkylene emulsifier. According to the disclosure, not only is compatibility achieved but this siloxane allows for matching of refractive indices for the continuous and discontinuous phases.

U.S. Pat. No. 5,280,019 (Klimisch) reports compositions which enhance the absorption and retention of moisturizer on the skin. These results are achieved through use of an organosilicon compound which is a carboxy functionalized polysiloxane or its metal carboxylate salt.

Evident from the foregoing art is that certain types of polysiloxanes incorporating hydrophilic functionality, e.g. polyoxyalkylene or carboxylate units, can assist in the emulsification of oily phases. Indeed these disclosures suggest the requirement for hydrophilic functionality on the silicones. Incorporation of hydrophilic groups for emulsification unfortunately detracts from the ability of silicones to provide a soft, silky afterfeel. These prior art hydrophilic silicones also do not fully solve oil and water phase compatibility problems. New systems are needed to carry relatively high levels of aqueous based moisturizing ingredients (e.g. glycerin). Also necessary are silicones that can achieve a smoother emulsion break to maximize positive sensory/feel attributes when the emulsions are rubbed into the skin. Anhydrous systems of occlusives are also not benefitted from hydrophilic bearing silicones which often lead to phase separation.

Accordingly, it is an object of the present invention to provide a skin treatment composition which is anhydrous yet provides improved skinfeel properties.

Another object of the present invention is to provide a skin treatment composition which has stability against phase separation even under freeze/thaw cycling.

Still another object of the present invention is to provide a skin treatment composition which achieves a smooth non-draggy rub-in upon initial application to the skin.

These and other objects of the present invention will become more readily apparent from consideration of the following summary and detailed description.

SUMMARY OF THE INVENTION

A skin treatment composition is provided which includes:

(i) from 0.1 to 30% of a crosslinked non-emulsifying siloxane elastomer;

(ii) from 1 to 50% of a skin conditioning agent;

(iii) from 10 to 80% of a volatile siloxane; and (iv) from 0 to 5% of water.

Particularly preferred conditioning agents within the context of this invention are hydrocarbons such as petrolatum and moisturizing polyols such as glycerin. Cyclomethicones are the preferred volatile siloxanes. Elastomers of the present invention are formed from divinyl compounds, particularly siloxane polymers with at least two free vinyl groups, reacting with Si-H linkages on a polysiloxane backbone. Most preferred of the elastomers are dimethyl polysiloxanes crosslinked by Si-H sites on a molecularly spherical MQ resin.

The composition of the present invention is based upon the concept of using crosslinked siloxane elastomer in combination with skin conditioning agents of a sticky nature. Although not to be bound by theory, it is believed these conditioning agents (when hydrophilic) are delivered in an internal phase of the mixture of elastomer and volatile siloxane. The latter acts as the external phase while dispersing an otherwise insoluble crosslinked siloxane elastomeric powder. Upon application of this system to the skin, the volatile siloxane evaporates leaving behind functional materials more compatible with skin fluids which become entrapped in the upper layer of the stratum corneum. Siloxane elastomer, not being compatible with these body fluids, remains on the surface of the skin. Since this elastomer is completely dispersed in the volatile siloxane, it is deposited in a very uniform layer on the skin. The thick three-dimentionally crosslinked siloxane elastomer film now functions as a layer between the insoluble aqueous/lipid context of the skin and the external environment. This mechanism masks negative feel characteristics of high levels of hydrophilic functional ingredients, such as glycerin.

DETAILED DESCRIPTION OF THE INVENTION

Now it has been found that crosslinked non-emulsifying siloxane elastomers in combination with skin conditioning agents and volatile siloxane result in a highly stable system and deliver an unusually soft, silky afterfeel to skin.

Crosslinked non-emulsifying siloxane elastomers are the first essential element of this invention. They will have an average number molecular weight in excess of 2,000, preferably in excess of 1,000,000 and optimally will range from 10,000 to 20 million. The term "non-emulsifying" defines a siloxane from which polyoxyalkylene units are absent. Advantageously the elastomers are formed from a divinyl compound, particularly a polymer with at least two free vinyl groups, reacting with Si-H linkages of a polysiloxane backbone such as a molecularly spherical MQ resin. Elastomer compositions are commercially available from the General Electric Company under product designation General Electric Silicone 1229 with proposed CTFA name of Cyclomethicone and Vinyl Dimethicone/Methicone Cross Polymer, delivered as 20–35% elastomer in a cyclomethicone carrier. A related elastomer composition under the CTFA name of Crosslinked Stearyl Methyl Dimethyl Siloxane Copolymer is available as Gransil SR-CYC (25–35% elastomer in cyclomethicone) from Grant Industries, Inc., Elmwood Park, N.J. The commercial products from General Electric and Grant Industries ordinarily are further processed by subjecting them to a high pressure (approximately 5,000 psi) treatment in a Sonolator with recycling in 10 to 60 passes. Sonation achieves a resultant fluid with elastomer average particle size ranging from 0.2 to 10 micron, preferably 0.5 to 5 micron. Viscosity is best when ranging between 300 and 20,000 cps at 25° C. as measured by a Brookfield LV Viscometer (size 4 bar, 60 rpm, 15 sec.).

Amounts of the elastomer may range from 0.1 to 30%, optimally from 1 to 15%, most preferably from 3 to 10% by weight.

A second essential element of the present invention is that of a skin conditioning agent. These agents may be selected from humectants, exfoliants or emollients.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. Amounts of humectant may range anywhere from 1 to 50%, preferably from 10 to 40%, optimally from 25 to 35% by weight.

Exfoliants according to the present invention may be selected from $C_2$–$C_{30}$ alpha-hydroxycarboxylic acids, beta-hydroxycarboxylic acids and salts of these acids. Most preferred are glycolic, lactic and salicylic acids and their ammonium salts. Amounts of the exfoliants may range from 1 to 15%, preferably from 2 to 10% by weight.

A wide variety of $C_2$–$C_{30}$ alpha-hydroxycarboxylic acids may be employed. Suitable examples of which include:

α-hydroxyethanoic acid
α-hydroxypropanoic acid
α-hydroxyhexanoic acid
α-hydroxyoctanoic acid
α-hydroxydecanoic acid
α-hydroxydodecanoic acid
α-hydroxytetradecanoic acid
α-hydroxyhexadecanoic acid
α-hydroxyoctadecanoic acid
α-hydroxyeicosanoic acid
α-hydroxydocosanoic acid
α-hydroxyhexacosanoic acid, and
α-hydroxyoctacosanoic acid When the conditioning agent is an emollient it may be selected from hydrocarbons, fatty acids, fatty alcohols and esters. Petrolatum is the most preferred hydrocarbon type of emollient conditioning agent. Other hydrocarbons that may be employed include mineral oil, polyolefins such as polydecene, and parafins such as isohexadecane (e.g. Permethyl 99® and Permethyl 101®).

Fatty acids and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids and alcohols.

Oily ester emollients may be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil.
2. Acetoglyceride esters, such as acetylated monoglycerides.
3. Ethoxylated glycerides, such as ethoxylated glyceryl monostearate.
4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
5. Alkenyl esters of fatty acids having 10 to 20 carbon atoms. Examples thereof include oleyl myristate, oleyl stearate, and oleyl oleate.
6. Ether-esters such as fatty acid esters of ethoxylated fatty alcohols.
7. Polyhydric alcohol esters. Ethylene glycol mono and di-fatty acid esters, diethylene glycol mono-and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.
8. Wax esters such as beeswax, spermaceti, myristyl myristate, stearyl stearate.

Amounts of the skin conditioning agent may range from 1 to 50%, preferably from 3 to 25%, optimally from 5 to 20% by weight.

A third essential element of the present invention is that of a volatile siloxane. The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon atoms, preferably containing from about 4 to about 5 silicon atoms, generally known as cyclomethicones. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes, the preferable range being from 0.1 to 8 centistokes. Examples of silicone oils useful in the present invention include: Dow Corning 244, Dow Corning 245, Dow Corning 344, Dow Corning 345 and Dow Corning 200 (manufactured by the Dow Corning Corporation); Silicone 7207 and Silicone 7158 (manufactured by the Union Carbide Corporation); SF1202 (manufactured by General Electric).

Amounts of the volatile siloxane will range from 10 to 80%, preferably from 20 to 70%, optimally from 30 to 65% by weight.

Cosmetic compositions of the present invention are essentially anhydrous. The amount of water will be confined to range from 0 to 5%, preferably not above 4%, more preferably not above 2%, optimally not above 0.5% by weight.

Beyond the basic components, other materials may be included depending upon the particular type of cosmetic composition sought. For instance, surfactants may be formulated into the compositions. These may be selected from nonionic, anionic, cationic or amphoteric emulsifying agents. They may range in amount anywhere from about 0.1 to about 20% by weight. Illustrative nonionic surfactants are alkoxylated compounds based on $C_{10}$–$C_{22}$ fatty alcohols and acids, and sorbitan. These materials are available, for instance, from the Shell Chemical Company under the Neodol trademark, Copolymers of polyoxypropylene-polyoxyethylene, sold by the BASF Corporation under the Pluronic trademark, are sometimes also useful. Alkyl polyglycosides available from the Henkel Corporation may also be utilized for purposes of this invention.

Anionic type surfactants include fatty acid soaps, sodium lauryl sulphate, sodium lauryl ether sulphate, alkyl benzene sulphonate, mono- and di-alkyl acid phosphates and sodium fatty acyl isethionate.

Amphoteric surfactants include such materials as dialkylamine oxide and various types of betaines (such as cocamidopiopyl betaine).

Minor adjunct ingredients may also be included such as fragrances, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

This Example illustrates an anhydrous skin treatment composition. Components listed in the Table below were added together in a vessel at 60° C. and mixed with a homogenizing agitator. Thereafter they were subjected to sonolation at 800–1,000 psi for five to ten minutes. The resultant product was a non-greasy semi-solid with a very silky afterfeel,

TABLE I

| COMPONENT | WEIGHT % |
| --- | --- |
| Petrolatum | 18.5 |
| Gransil SR-CYC | 30 |
| DC 344 Fluid ® | 51.5 |

EXAMPLE 2

This Example illustrates another anhydrous skin treatment composition according to the present invention. The formulation was prepared in a manner essentially similar to that of Example 1 utilizing the components listed in the Table below. The resultant product had a smooth, silky afterfeel.

TABLE II

| COMPONENT | WEIGHT % |
| --- | --- |
| Petrolatum | 22 |
| Gransil SR-CYC | 43 |
| DC 244 Fluid ® | 35 |

EXAMPLE 3

A series of experiments were performed to evaluate the effect of water upon compositions of the present invention. Formulations and performance characteristics are listed under Table III.

TABLE III

| COMPONENTS | CTFA NOMENCLATURE | FORMULATION (WEIGHT %) | | | |
| --- | --- | --- | --- | --- | --- |
| | | A | B | C | D |
| GE SE 1229 (25% elastomer in D4/D5 volatile silicone) | Vinyldimethicone/ Methicone Crosspolymer | 31 | 31 | 31 | 31 |
| Dow 345 Silicone fluid | Cyclomethicone | 31 | 38 | 35 | 26 |
| Dow 344 silicone fluid | Cyclomethicone | 8.5 | 8.5 | 8.5 | 8.5 |
| Petroleum Jelly | Petrolatum | 11 | 11 | 11 | 11 |
| Glycerin (DRY) | Glycerin | 8 | 8 | 8 | 8 |
| Abil EM90 | Cetyl Dimethicone | 0.5 | 0.5 | 0.5 | 0.5 |

TABLE III-continued

| COMPONENTS | CTFA NOMENCLATURE | FORMULATION (WEIGHT %) | | | |
|---|---|---|---|---|---|
| | | A | B | C | D |
| DI Water | Copolyol Demineralized Water | 0 | 3 | 6 | 15 |
| PERFORMANCE | | | | | |
| Initial Feel Upon Application To Skin | | BEST | GOOD | NOT GOOD | NOT GOOD |
| | | non traditional smooth/silky "powdery" application non draggy upon rub in | non traditional smooth/silky "powdery" application slightly draggy upon rub in | more traditional losing "powdery" transition upon application to draggy upon rub in | traditional rub in transition upon application very draggy upon rub in |
| Phase Stability (Freeze/Thaw) | | Pass | Pass | Fail | Fail |

Results of the experiments in Table III indicate that formulations containing 6% water fail in the freeze/thaw cycling stability evaluation. Moreover, the skinfeel of the product upon initial application demonstrates that at 6% water, there is a draggy sensation upon rub in. By contrast, at 0% water a smooth rub in was observed. When 3% water was present, there was only a slightly draggy feel.

The foregoing description and Examples illustrate select embodiments of the present invention. In light thereof, various modifications will be suggested to one skilled in the art, all of which are within the purview and spirit of this invention.

What is claimed is:

1. A semi-solid skin treatment composition consisting essentially of:
   (i) from 0.1 to 30% of a crosslinked non-emulsifying siloxane elastomer formed from a divinyl compound reacted with Si-H linkages of a polysiloxane;
   (ii) from 1 to 50% of a skin conditioning agent which is a polyol;
   (iii) from 30 to 80% of a volatile siloxane; and
   (iv) from 0 to 5% of water.

2. The composition according to claim 1 further comprising a material selected from the group consisting of exfoliants, emollients and mixtures thereof.

3. The composition according to claim 2 wherein the emollient is a hydrocarbon.

4. The composition according to claim 3 wherein the hydrocarbon is petrolatum.

5. The composition according to claim 1 wherein the the polyol is selected from the group consisting of glycerin, propylene glycol, polyethylene glycol and mixtures thereof.

6. The composition according to claim 2 wherein the exfoliant is selected from the group consisting of alpha-hydroxycarboxylic acid, beta-hydroxycarboxylic acid and salts thereof.

7. The composition according to claim 1 wherein water is present from 0 to 3% by weight.

* * * * *